(12) United States Patent
Gurley

(10) Patent No.: US 6,553,243 B2
(45) Date of Patent: Apr. 22, 2003

(54) COMMUNICABLE DISEASE BARRIER METHOD OF USE

(76) Inventor: Mariruth D. Gurley, 6956 Oro Bangor Hwy., Oroville, CA (US) 95966

( * ) Notice: Subject to any disclaimer, the term of this patent is extended or adjusted under 35 U.S.C. 154(b) by 71 days.

(21) Appl. No.: 09/754,967

(22) Filed: Jan. 4, 2001

(65) Prior Publication Data

US 2001/0002431 A1 May 31, 2001

Related U.S. Application Data

(62) Division of application No. 09/233,284, filed on Jan. 19, 1999, now Pat. No. 6,179,159.
(60) Provisional application No. 60/072,594, filed on Jan. 26, 1998.

(51) Int. Cl.[7] .................................................. A61B 5/00
(52) U.S. Cl. ....................................... 600/340; 600/344
(58) Field of Search ................................ 600/310, 322, 600/323, 340, 344; 206/305, 306, 438

(56) References Cited

U.S. PATENT DOCUMENTS

| | | |
|---|---|---|
| 2,438,901 A | 5/1948 | Coxe |
| 4,773,532 A | 9/1988 | Stephenson |
| 4,863,084 A | 9/1989 | Nabozny |
| 5,044,494 A | 9/1991 | Tamura |
| 5,209,230 A | 5/1993 | Swedlow et al. |
| 5,413,101 A | 5/1995 | Sugiura |
| 5,452,717 A | 9/1995 | Branigan et al. |
| 5,619,992 A | 4/1997 | Guthrie |
| 5,740,943 A | 4/1998 | Shields et al. |

Primary Examiner—Eric F. Winakur

(57) ABSTRACT

A disposable digit cover structured to be applied to envelop a portion of a human finger or toe, i.e., digit, for aiding in prevention of the spread of communicable diseases and cross-patient contamination from pulse oximeter probes. The cover is a flexible, tubular structure of material impervious to the passage of infectious agents, and having an open end, a closed end and being sufficiently transparent to light to serve as a barrier between a human digit and a pulse oximeter probe. The barrier is first placed over the digit, the medical probe is then clamped on the barrier to pass light into the digit. The readings are taken, the probe is removed, then the barrier is removed and discarded.

4 Claims, 5 Drawing Sheets

COMMUNICABLE DISEASE BARRIER METHOD OF USE

CROSS-REFERENCE TO RELATED APPLICATIONS

This Application is a Rule 1.53 Divisional application of U.S. application Ser. No. 09/233,284 filed Jan. 19, 1999, now U.S. Pat. No. 6,179,159 issued Jan. 30, 2001, and a 35 USC 120 priority claim is made for this Application to the effective date of U.S. application Ser. No. 09/233,284 which made a priority claim to U.S. Provisional application No. 60/072,594 filed Jan. 26, 1998.

BACKGROUND OF THE INVENTION

1. Field of the Invention

The present invention generally relates to barrier type covers useful on human patients for aiding in prevention of the spread of communicable diseases, and is particularly directed toward a method of using a digit (finger or toe) covering barrier and pulse oximeter probe.

2. Brief Description of the Related Prior Art

U.S. Pat. No. 5,619,992 issued Apr. 15, 1997 to R. B. Guthrie et al describes a sheath/cover made of infectious agent impervious material, and which is flexible and transparent to passage of light from a pulse oximetry sensor. Pulse oximetry sensors are also referred to as pulse oximeter probes, the various structures and operation of which is well known. The Guthrie et al cover is structured for, and always described as, being for location over or surrounding the probe and over part of the probe electrical line. Guthrie et al do not appear to recognize that the odd shape of a pulse oximeter probe with the attached electrical line renders it more difficult and time consuming to apply (and remove) a disease barrier cover over the probe and line, as compared to placing a barrier cover over the relatively straight diameter of a finger (or toe) of the patient as herein described in reference to the present invention. Furthermore, Guthrie et al appear to fail to describe or mention any type of efficient, low cost packaging for their sensor cover. Guthrie et al do however appear to recognize that many if not most pulse oximeter probes currently in use in the U.S. appear to be of the "reuseable" type which if unprotected when used on a patient should be cleaned prior to use on another patient, such cleaning of reuseable sensors dramatically increasing the cost of use, and thus many are simply used uncleaned between patients.

U.S. Pat. No. 5,209,230 issued May 11, 1993; U.S. Pat. No. 5,413,101 issued May 9, 1995; and U.S. Pat. No. 5,452,717 issued Sep. 26, 1995 all teach what are stated to be pulse oximeter probes sufficiently inexpensive to be disposed of after use on a patient. Such disposable pulse oximeter probes are intended to prevent cross-patient contamination and also to eliminate the costly process of having to clean a reuseable type probe between use on each patient. However, due to the cost of optical light emitters and optical detectors, electrical wires and the other parts associated with such disposable probes, disposal of such sensors (probes) after each use is not likely to be the most economical method of preventing cross-patient contamination which can be devised.

U.S. Pat. No. 2,438,901 issued Apr. 6, 1948 to C. D. Coxe describes a finger cot or sheath which is flexible, transparent and made of plastics. The Coxe disclosure does not mention utilizing the sheath with a pulse oximeter probe for reducing cross-patient contamination by the probe, nor is there a mentioning of an inexpensive and efficient dispensing packaging for the sheaths.

It is believed that there exists a significant need for a more economical and yet convenient arrangement of preventing cross-patient contamination from the use of reuseable pulse oximeter probes.

SUMMARY OF THE INVENTION

The present invention addresses the need for a more economical and yet convenient arrangement of preventing cross-patient contamination from the use of reusable pulse oximeter probes, or similar digit-attachable light emitting/reliant medical probe. The present invention includes a sheath-like cover in the form of an infectious agent barrier structured to be applied to a human finger or toe, i.e., digit, for aiding in prevention of the spread of communicable diseases (infectious agents) from the patient to a reuseable pulse oximeter probe, or from the probe to the patient. The cover is a barrier against infectious agents such as viruses, bacteria, transferable infections or other abnormal body conditions that would impair normal bodily function and which can be spread by contact with another person or object. The invention further includes a dispensing package useful for holding and conveniently dispensing such covers in a clean condition and ready for use.

A main object of the present invention is to decrease the incidence of nosocomial infections in a medical clinic, doctor's office or in a hospital setting by providing a suitable and disposable digit cover intended for use between a reuseable pulse oximeter probe and a human digit, and serving as an infectious agent barrier between the digit and probe.

A further object of the invention is to provide such a cover in a convenient to use arrangement allowing convenient storage, transportation and access to the covers for providing a low cost of use.

A further object of the invention is to provide such a cover structured to be inexpensively manufactured and sold inexpensively so that the covers can be more economically disposed of after use on a patient compared to being cleaned and reused, and thus are clearly disposable digit covers.

A further object of the invention is to provide such a cover in a package containing a plurality of covers structured for the ready separation of one cover from the others and the ready acquisition of a single cover at a time.

A further object of the invention is to provide the package containing the covers in a structure allowing the convenient transportation and storage thereof in a garment pocket of a health care worker, or the hanging thereof on a hook or clipboard adjacent a patient bed or storage in a drawer so that little time is spent looking for or accessing the covers when needed.

An even further object is to provide the package containing the covers in an inexpensive structure allowing for the package, when empty, to be economically disposed of rather than be refilled with more covers.

An even further object is to provide the package in a structure which aids in maintaining the covers therein suitably clean and mechanically protected against damage.

A still further object is to provide such a combination dispensing package with removable digit covers in a structural arrangement which is sufficiently inexpensive to manufacture and thus to purchase, and sufficiently quick and easy to use (low labor costs associated with use) in a patient care setting, that the use thereof is very much encouraged because of the significant benefits and ease of use.

A further object of the invention is to provide such a combination dispensing package with removable digit covers for use in conjunction with a reuseable pulse oximeter probe so as to greatly reduce the needed frequency of cleanings of the oximeter probes in those medical facilities which are currently concerned about cross-patient contamination from such probes and which are expending time to clean such probes.

These, as well as other objects and advantages of the present invention will become more apparent with continued reading and with a review of the included drawings wherein the principles of the invention are described in reference to an exemplary structural embodiment shown in the drawings.

BEST MODES FOR CARRYING OUT THE INVENTION

Figure 1:
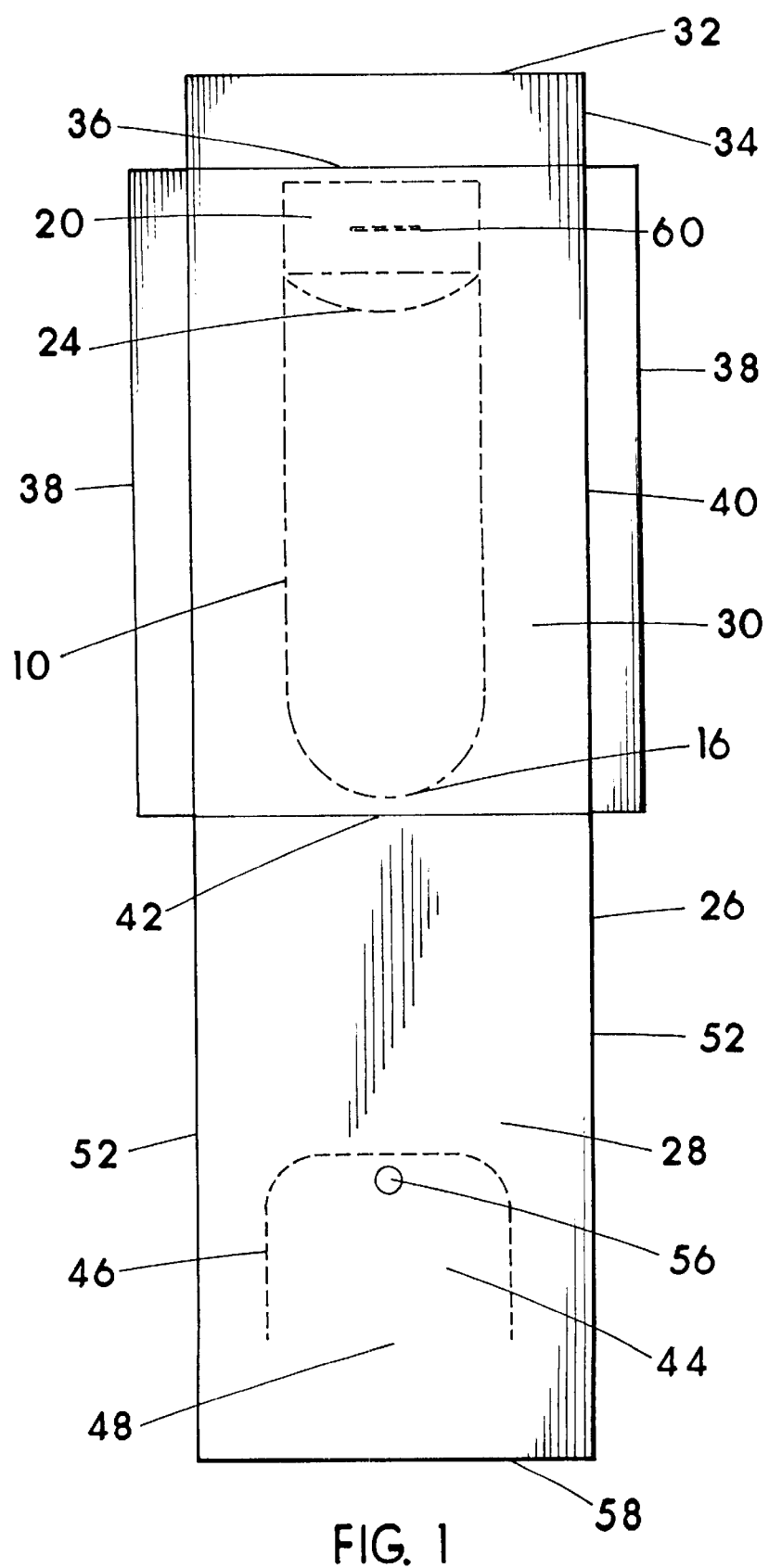
FIG. 1 shows a blank of material such as heavy paper cut in preparation of folding into a dispensing package for holding digit covers in accordance with the present invention. The broken lines in the upper area of the blank represents the location at which the digit covers are to be installed. The broken lines in the lower area of the blank represent a perforated tearable portion in the material for defining a dispensing opening and door-like flap.

In furtherance of the details provided in the above Summary of the Invention, and the objects of the invention stated therein, I will now proceed with a detailed description of the invention while making specific reference to the drawing figures showing a preferred embodiment and portions of the embodiment in accordance the present invention. I will describe the invention from both a preferred structural and methodology standpoint, and it should be noted that some changes in that herein described can clearly be made without departing from the true scope of the invention, as the herein description is of best modes and preferred embodiments which are not intended to strictly limit the scope of the invention.

The present digit cover 10 is particularly directed toward use as an infectious agent barrier between a human digit, i.e., finger 66 or toe 78, and a reuseable pulse oximeter probe 68 of the probe type attachable to a human digit and which aids in detecting the pulse of the patient, or the blood oxygen level of the patient, or both the pulse and oxygen level (which is most common), utilizing, emitted light passed through the digit from one jaw of the probe and received on the other side of the digit by an optical receiver on another jaw of the probe. The probe is wired to probe monitoring equipment. The structures of, and operation of pulse oximeter probes (sensors) and probe monitoring systems and equipment to which the probe is connected are well known and in wide use across the U.S. in medical facilities, and therefore I will not herein describe in great detail such widely known and used equipment and information, although some of the above cited prior art documents do provide some additional information which may be of value to those interested readers unfamiliar with such medical equipment.

Figure 5:
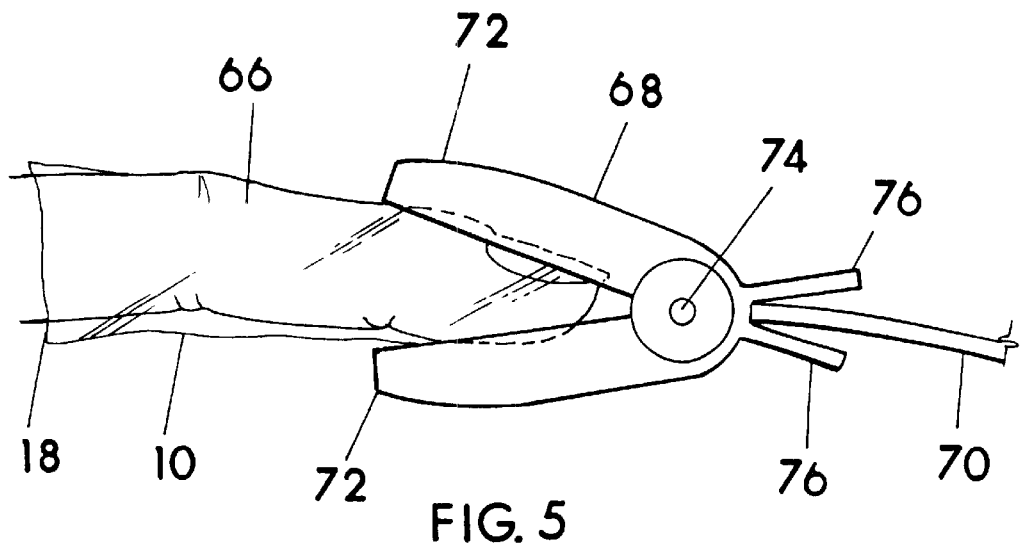
FIG. 5 shows a reuseable pulse oximeter probe attached to a human finger, and a cover in accordance with the present invention located over the finger and serving as a barrier between the finger and the probe.
Figure 6:
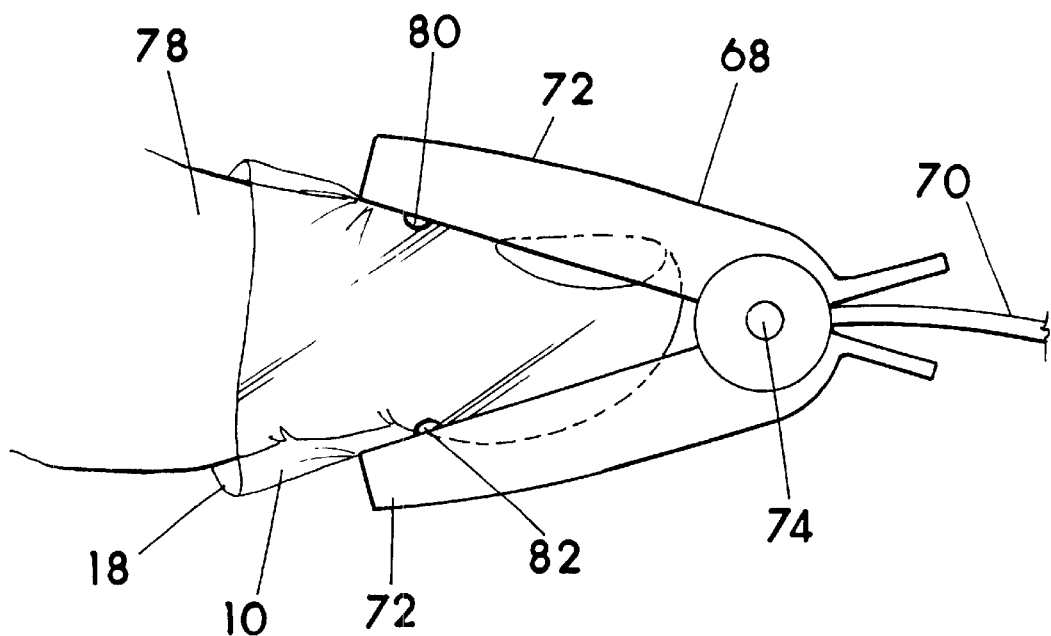
FIG. 6 shows a pulse oximeter probe attached to a human toe, and a cover in accordance with the present invention over the toe and serving as a barrier between the toe and the probe.

The present digit cover 10 is structured to be applied to envelop or surround a portion of a human digit which could contact the jaws 72 or any other part of a pulse oximeter probe 68, particularly the distal end of the digit since typically the probe 68 is attached to the digit in the distal area thereof as shown in FIGS. 5 and 6. The covers 10 could be sized to cover the entire length of the digit if desired. The covers 10 can be made in different lengths and diameters for fitting toes and fingers, although only one size should probably be in a given package 26, and one cover 10 sized to adult fingers should function well with any adult fingers since a loose fit is acceptable. Children and baby sizes could be made, and well as a shorter length version for use on toes. An example of a reasonable size of cover 10 for adult fingers would be 3 inches in total length with the extending portion 20 being about ½ inch of the total, and 1½ inches wide when in the flattened stored condition, with these dimensions being for example only. For ease of application to the digit and so that a given size of cover 10 can fit differing length and diameters of human digits, covers 10 can be and are preferably loose fit over the digit (a single digit), as material from which covers 10 are made is flexible, and the jaws 72 of the probe 68 typically being urged closed by a spring member at pivot 74 (see FIGS. 5 and 6) will press the material of cover 10 against the digit and allow proper operation. As shown in FIG. 5, probes 68 typically include finger tabs 76 on the far side of pivot 74 to allow the opening of the jaws 72, and additionally include an electrical wire 70 connected for providing electrical power to light emitter 80 of the probe and for feeding information from the light receiver 82 (see FIG. 6) back to the probe monitoring system from which wire 70 came.

Cover 10 is a flexible, tubular structure which can be made and used as a generally straight or single diameter tube having an open end 18 for entrance of the digit into the tubular interior, and an oppositely disposed end which is preferably a closed end 16 to prevent the unintentional protrusion of the digit therefrom. The cover 10 is made of infectious agent impervious material, which is also fluid impervious, such as thin transparent plastics, e.g., polyethylene, vinyl, cellulose acetate, etc., and the material is sufficiently thin and transparent to light, at least the light emitted by the oximeter probe, to allow serving as a barrier between a human digit and a pulse oximeter probe 68.

The tubular structure of the covers 10, which is preferably flattened when stored in package 26 for more compact storage, can be formed by numerous processes, and can be formed by stamping or cutting material and by heat or sonic or adhesive bonding or the like of the peripheral side edges of front panel 12 to the peripheral side edges of back panel 14, and also closing the closed end 16 of the cover with the same bonding or seaming process. Closed end 16 could be a fold in a single strip of plastics or the like film which is folded to define the closed end 16 and seamed along the lateral sides to form the tubular structure, an arrangement wherein the fold would be transverse to the length of the material strip, and off-center so that a terminal edge 24 of front panel 12 would be downward from the somewhat adjacent terminal edge of back panel 14, thereby a further extending portion 20 of the back panel 14 would be created. Molding techniques of various types could also be used, and seams at the sides are not required to form a tubular structure.

The covers 10 are expandable from the flattened stored condition with the insertion of a human digit, much like a plastic food handling glove, such gloves commonly stored in a flattened condition. The covers 10 each preferably include front panel 12 with terminal edge 24 at the open end 18 and positioned adjacent further extending portion 20 of back panel 14, the front panel 12 terminal edge 24 for allowing the ready insertion of a finger tip or toe into the cover 10 by sliding along the back panel until edge 24 is engaged at which point the digit tip being somewhat ramped shaped usually slips under edge 24 and can be slid into the tubular interior of the cover 10. When the edges of the cover 10 are uneven, it is simply easier to separate the edges to allow the insertion of a finger or toe into the interior. Such an arrangement also allows the grabbing of the front panel 12 between the index finger and the thumb, pinching the material of front panel 12 in the area of terminal edge 24 with the tip of the index finger either under edge 24 or causing the material to roll upward in a wrinkle which can be pinched between the finger for pulling a single cover 10 from the dispensing package 26. Dispensing package 26 will be described below, but at this point I will state that the opening 54 in the dispensing package 26 is preferably positioned such that when open (flap 44 is raised as in FIG. 4), the portion of the uppermost cover 10 exposed through the opening should be the front panel 12 portion with terminal edge 24 exposed for grasping or withdrawal of a cover from the package 26 since the covers 10 are flexible and can bend and distort, and in effect be extracted through a small hole. The flexible covers 10 also allow movement of a digit covered by a cover 10. The entire front panel 12 does not need to be exposed, and leaving the bottom or closed end 16 covered by package 26 helps maintain the remaining covers 10 in the stack both stationary and clean. The health care worker should have clean hands or gloves when handling both the package 26 and covers 10, and I will state at this time that even with the proper use of covers 10, a reuseable probe 68 should be periodically cleaned and sanitized, for example, every so often depending on the number of patients on which the probe has been used.

Figure 2:
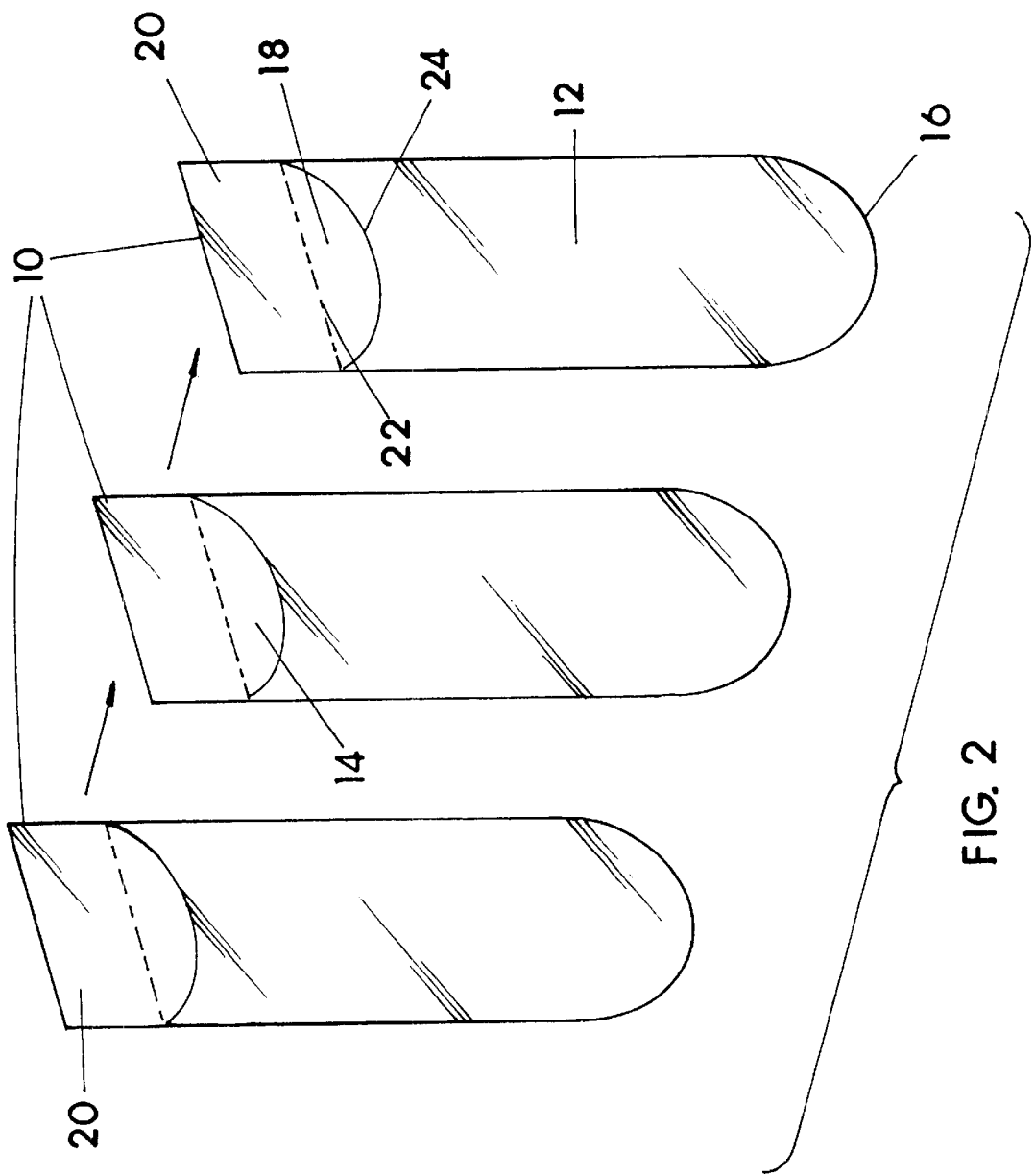
FIG. 2 shows a plurality of identical covers in accordance with the present invention in the process of being stacked.

The further extending portions 20, which could also be called securement portions, of the back panels 14 of the covers 10 when packaged are aligned (stacked) one atop the other and secured stationary to the package 26 such as with a mechanical fastener such as a staple 60 as indicated in FIG. 1. The covers 10 preferably include a scoring or perforations 22 (see FIGS. 2 and 4) adjacent the open end 18 in the back panel 14 allowing the dependable tearing of the covers 10 from securement to the package 26, one cover 10 at a time, and in some cases the staple 60 will by the fact that it perforates the extending portion 20 allow the material to be dependably torn at the staple, scoring or perforations. The tear off line 22 should be positioned in back panel 14 above terminal edge 24 of front panel 12 so that a portion of back panel 14 is left extending beyond edge 24 after the cover 10 has been removed from package 26. The tearing of a cover 10 from package 26 leaves a portion of the extending portion 20 of back panel 14 remaining beneath the fastener or staple 60. The covers 10 are stored and transported in factory clean or sterile state in a flattened compact and stacked condition within a dispensing package 26 containing a plurality of covers 10 which can be accessed when a door or flap 44 of the package 26 is in the open position. It should be noted the although gloves used for major surgery in the U.S. are sterile, most latex, vinyl and the like groves used in the medical and dental industry in the U.S. are not sterile from the packaging, but are instead factory clean, which at least at this time is apparently considered sufficient for most applications other than major surgery. Typically, the process of manufacturing plastic and latex items uses heat which destroys infectious agents. Thin, plastic film food-handling gloves are also typically just factory clean and are usually considered clean enough for handling food for human consumption. The present covers 10 can be packaged factory clean, or can be packaged sterile in a sterile package 26, or packaged and then sterilized as a unit. It should be noted that I have successfully made a functional digit cover facsimile used with a probe 68 by simply cutting off a finger portion of a transparent thin-film plastic food handling glove, and slipping the glove tubular finger portion over the finger or toe followed by applying the probe 68 in the usual manner to the plastic covering the digit, and the probe functioned properly. Although a simple structure such as a plastic glove finger as described above functions to meet some objectives of the invention, as herein described, the preferred cover should have additional means for aiding in getting the cover open for application on the digit. Among other aspects including structuring allowing packaging and therefore efficient transportation, storage and use of the cover 10.

Figure 3:
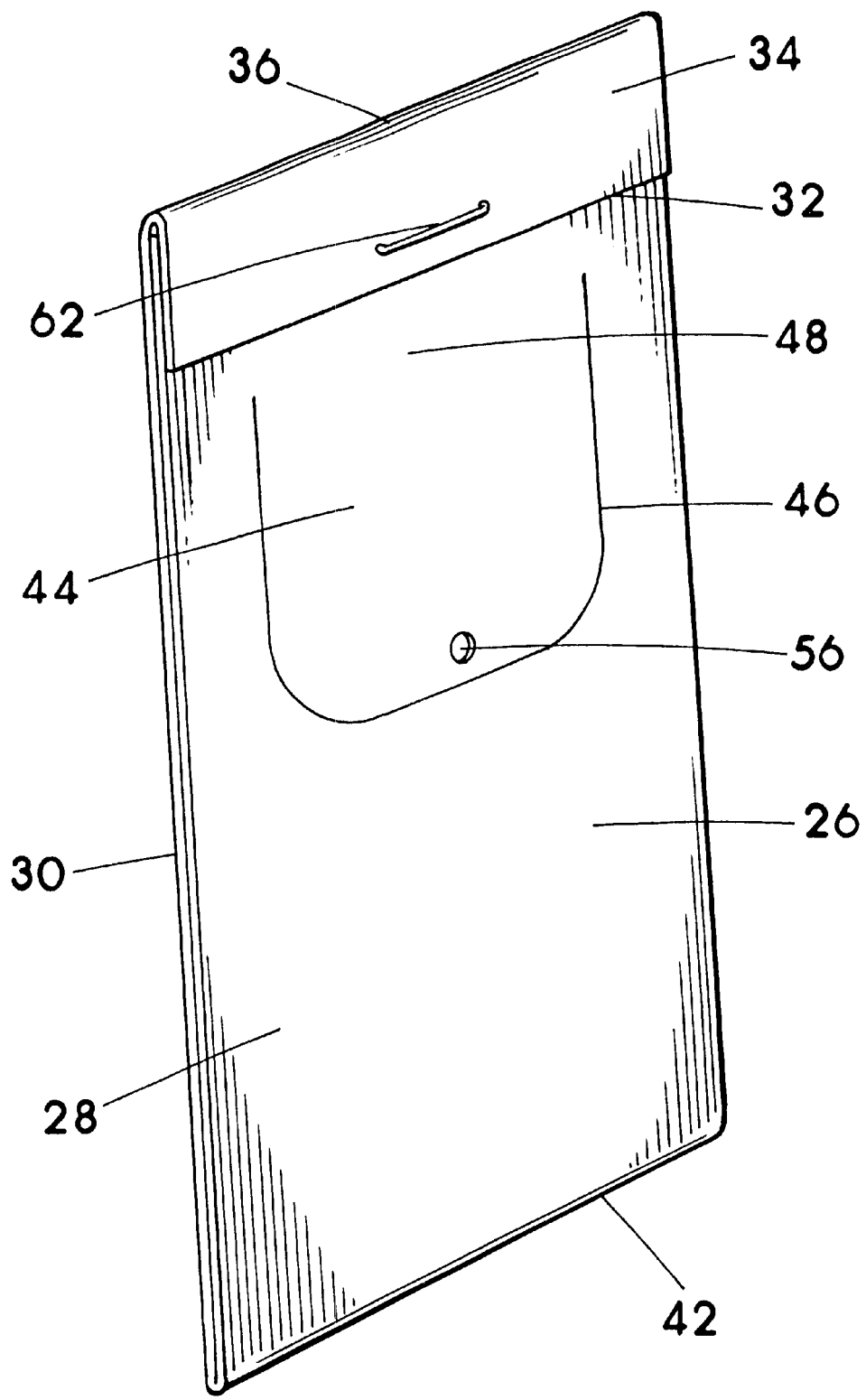
FIG. 3 shows the blank of FIG. 1 folded into a dispensing package and in the closed position.
Figure 4:
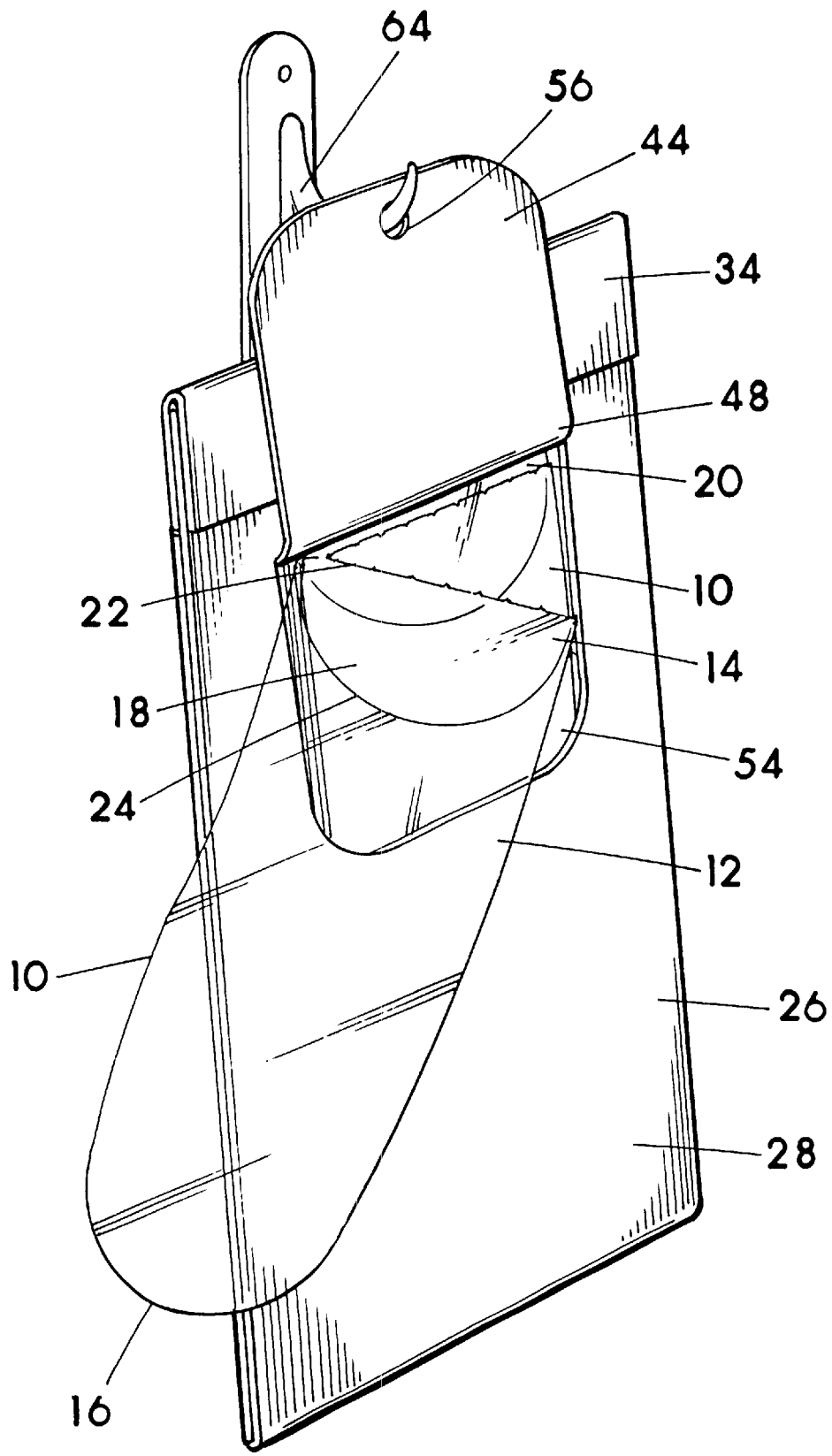
FIG. 4 shows the package of FIG. 3 in an open position with the flap raised with one digit cover in the process of being removed. A human hand which would be the instrument for removing the cover is not shown in the drawing for the sake of clarity of that which is shown.

With reference mainly to FIGS. 1, 3–4. Dispensing package 26 for containing a plurality of covers 10 is preferably sufficiently small to be readily carried in a garment pocket of a health care worker. I would say the outer dimensions should be under 8 inches long, under 5 inches wide and under two inches thick, and the package actually could be about one-half these dimensions in most cases, and probably only ¼ inch thick or so depending upon the number of covers 10 to be stored in stacked fashion therein. I would think anywhere from 10 to 100 covers per package 26 would be reasonable. The resulting size of package 26 can be varied dependant upon approximate rate of use. Package 26 serves the purposes of maintaining the covers 10 in an organized fashion; physically or mechanically protects the covers, and helps maintain the cleanliness of the covers 10. Package 26 should be made inexpensively so that it can be disposed of when all of the covers 10 have been used. The package 26 is or should be sufficiently inexpensive to be disposed of along with a few covers 10 remaining therein should it become prematurely soiled, and so inexpensive that the labor cost of refilling the package 26 in a health care facility is too high to justify such refilling (and cleaning) compared to the cost of purchasing a new package 26 with covers 10 therein, and this due to factories, such as those who would manufacture the present invention, typically being very efficient at repetitive manufacturing of like items. For example, few if anyone would attempt to profitably refill a paper matchbook with new paper matches. It is simply far easier and cost and time efficient to buy a new matchbook. Likewise, package 26 is intended to be the same situation. Therefore, the exterior material defining an interior chamber for container covers 10, shown in a cut material blank in FIG. 1, can be made of paper, such as matchbook like or type paper, or any other suitable paper or material, it could be thinner or thicker, which can be inexpensively die cut with available and known machinery. Specific cutting-dies will be needed for the blank shown in FIG. 1. Package 26 could be made of other materials such as sheet stock made of plastics for example, but this will probably cost more, and is not likely to take a fold or to accept glues as well as a paper sheet or blank.

FIG. 1 shows a blank of material such as paper, in a single piece, cut in preparation of folding into dispensing package 26 for holding and dispensing digit covers 10 in accordance with the present invention. The broken line figure in the upper area of the blank represents the location at which the digit covers 10 are to be installed in an aligned and stacked fashion. A staple 60 is shown to illustrate the location where the staple is applied through a stack of aligned extending portions 20 to secure the extending portions stationary and securely to what is in effect the inside surface of the back side 30 of package 26. The blank of foldable material is shown as a flat rectangular piece having a top edge 32, a bottom edge 58, two oppositely disposed lateral side edges 52, a central transverse fold line or score 42 which is slightly off-center, an upper fold line or score 36 with a panel 34 defined between line 36 and top edge 32, two oppositely disposed narrow fold-over side panels 38 with fold scores or lines 40 where the panels 38 join the main body portion at edges 52; a three-sided perforation 46 for defining a flap 44 which when punched out on the three sides along perforations 46, in effect creates an opening 54 through the material (through the front exterior of the package 26) and provides a closeable and openable door over opening 54. Opening 54 is shown in FIG. 4. Material is left along one side of flap 44 with this flexible material indicated as area 48 serving as a hinge allowing the manual repositioning of the flap for accessing the covers 10 and for closing the opening. A hole 56 is shown in flap 44 for receiving a hanging hook 64 anchored to a wall, cabinet or the like in the medical facility. The hanging being possible when the flap 44 is opened, although a separate loop or hole bearing piece could be attached to package 26 so it could be hung on a hook with the flap 44 closing the packaging opening 54. Also shown is the portion of the blank which will become in effect the back side 30 of the package 26. The portion of the blank which will become in effect the front side of the package is indicated with 28. The blank can be cut and perforated very efficiently and inexpensively using modern machinery.

After the blank is cut and perforated to the form shown in FIG. 1 (or some other suitable form), a stack of covers 10 can be stapled to the inside surface of back panel 30 as indicated in FIG. 1. The two narrow side panels 38 are folded inward at lines 40 toward the covers 10 to lay atop panel 30 and which may be partly atop the lateral side edges of the covers 10. Then front panel 28 is folded up to back panel 30 at fold line 42 so as to lay atop the outer facing surface of side panels 38 and covering the covers 10. The lateral inside edges of front panel 28 can be glued or stapled to the adjacent narrow side panels 38 or left unattached depending upon how well the folding remains without attachments. Then the top panel 34 is folded downward atop the upper edge 58 of front panel 26, covering edge 58, and is glued or stapled thereto such as with a staple 62 as shown in FIG. 3. Staple 62 can also be used to hold the covers 10 secured to the package 26 possibly eliminating the need for staple 60. The staples, if used, should be applied so that sharp ends which could snag clothing or flesh should be turned inward and buried in the paper. Side panels 38 aid in preventing covers 10 from angling sideways and extending out the sides of package 26, but depending upon the stiffness of the material defining covers 10, and possibly the distance of the nearest edge of the covers to the sides of the package 26, the side panels 38 could be eliminated wherein the sides would be left open much like a book of paper matches for starting fires.

A new and still sealed package 26 can be manually opened by flexing enough to allow pressing a finger inward along a perforated line at the peripheral edge of flap 44 so as to tear open the perforation 46, slip a finger in and release all three sides of the perforation 46 allowing flap 44 to be bent upward to expose package opening 54 which as mentioned earlier exposes the top or upper most cover 10 in the area of terminal edge 24 of front panel 12. This allows the grasping or pinching of the cover 10 between a finger and a thumb and the tearing of the cover 10 from its securement to package 26. The cover 10 can then be applied on the selected digit of the patient, the pulse oximeter probe applied to the cover 10 and the patient monitored, followed by removing the probe, then removing the cover 10 and disposing of the used cover.

Since the covers 10 can be of a loose fit on the digit as mentioned above, the probe should not be placed on thick wrinkling in the cover, but the wrinkling should be pulled up or down out of the probe attachment zone. Care should be taken to not contact the probe against the patient. The flap 44, once open, should be closeable, allowing it to remain closed or closed enough due to some anticipated misalignment and engagement of and between extending remnants of the material between the perforations 46 on both the main body of package 26 and flap 44. A closing clasp of some suitable type could be added if desired.

Having described the covers 10 and packaging 26 above in great detail for example, and having made many statements in reference to the uses, applications, methods and objects thereof, at the risk of being redundant but for the sake of positive clarity, methodology with the structures for carrying out the methodology is set forth below.

The present invention from one viewpoint can be viewed as a method or including a method of reducing infectious agent transmission from a human digit onto a pulse oximeter probe (medical probe) or from the probe to the digit, for reducing cross-patient contamination, and generally comprises the steps of:

(a) removing, from a dispensing package which contains a plurality of digit covers stored therein, a single digit cover made of infectious agent impervious material which is flexible and transparent permitting the passage of light emitted by a pulse oximeter probe; and then (b) locating the flexible and transparent digit cover over a distal end of a human digit of a patient to be monitored; and followed by (c) applying jaws of a pulse oximeter probe to the digit cover located over the human digit so that the jaws of the probe contact only the digit cover and do not come in contact with the patient; and locating the jaws in the proper normal location on the digit for proper functioning thereof; and which begins the (d) monitoring the patient's condition using the pulse oximeter probe until monitoring with the probe is complete;

(e) removing the pulse oximeter probe from the patient without touching the jaws of the probe against the patient, as touching the probe against the patient further increases the risk of cross-patient contamination; and then (f) removing the digit cover from the digit of the patient; followed by (g) disposing of the digit cover removed from the patient; and preferably, washing one's hands. The same steps should be followed on the next patient needing monitoring with the pulse oximeter, or repeated on the same patient the next time the patient needs checking.

All of the above procedures using the pulse oximeter probe and digit cover should be completed by the health care worker using the universal precautions of washing their hands to avoid contamination of the digit cover and/or physically spreading a communicable disease.

Clearly the steps could be stated in other ways, and more steps or details or fewer steps and details for each step could be recited, but it is believed the methodology and structures to be manipulated as above stated and can be gleaned from this disclosure as a whole are at this point clear and understandable to one of ordinary skill having read or studied this disclosure.

Having described the principles of the invention in detail with reference to an exemplary structural embodiment shown in the drawings, it will be, upon a reading of this disclosure, readily apparent to those skilled in the art that some changes in that herein described can clearly be made without departing from the true scope of the invention as recited in the claims.

I claim:

1. A method of reducing infectious agent cross-patient contamination from use of a pulse oximeter probe, comprising the steps of:
   (a) firstly removing, from a dispensing package sized to fit in a garment pocket, a single clean digit cover, the digit cover made of flexible material which is impervious to passage of infectious agents and which is transparent to light passage of light emitted by a pulse oximeter probe;
   (b) secondly locating said digit cover over a human digit of a patient to be monitored, and followed by
   (c) thirdly applying jaws of a pulse oximeter probe to said digit cover located over the human digit so that the jaws of the probe only contact said digit cover and do not contact the patient;
   (d) fourthly monitoring the patient's condition using the pulse oximeter probe until monitoring with the probe is complete;
   (e) fifthly removing the pulse oximeter probe from the patient absent touching the jaws of the probe against the patient;
   (f) sixthly removing said digit cover from the digit of the patient; and then
   (g) disposing of said digit cover removed from the patient.

2. A method of reducing infectious agent cross-patient contamination from use of a pulse oximeter probe, comprising the steps of:
   (a) firstly locating a clean digit cover over a human digit of a patient to be monitored; said digit cover made of flexible material which is impervious to passage of infectious agents and which is transparent to light passage of light emitted by a pulse oximeter probe; and then followed by
   (b) secondly applying jaws of a pulse oximeter probe to said digit cover located over the human digit so that the jaws of the probe only contact said digit cover and do not contact the patient; and then followed by
   (c) thirdly monitoring the patient's condition using the pulse oximeter probe until monitoring with the probe is complete.

3. A method according to claim 2 further including the steps, following the monitoring the patient's condition step, of:

removing the pulse oximeter probe from the patient; and then removing said digit cover from the digit of the patient; and then disposing of said digit cover removed from the patient.

4. A method of reducing infectious agent contamination from use of a medical probe, comprising the acts of:
   (a) firstly locating a clean digit cover over a human digit of a patient to be monitored with a probe; said digit cover made of material which is impervious to passage of infectious agents and which is transparent to light passage of light used by a probe, and then
   (b) secondly applying the medical probe to said digit cover located over the human digit, and then
   (c) thirdly monitoring the patient's condition using the probe, followed by
   (d) fourthly removing the probe from the patient and then
   (e) fifthly removing said digit cover from the digit of the patient and then
   (f) finally, disposing of said digit cover.

* * * * *